United States Patent
Sugi et al.

(10) Patent No.: US 7,208,645 B2
(45) Date of Patent: Apr. 24, 2007

(54) PROCESS FOR PRODUCING 4-(2-METHYLPHENYL)BENZOTRIFLUORIDE

(75) Inventors: Kiyoshi Sugi, Osaka (JP); Masahide Tanaka, Nishinomiya (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/370,985

(22) Filed: Mar. 9, 2006

(65) Prior Publication Data

US 2006/0211896 A1 Sep. 21, 2006

(30) Foreign Application Priority Data

Mar. 11, 2005 (JP) ............................. 2005-069785

(51) Int. Cl.
C07C 17/26 (2006.01)
C07C 19/08 (2006.01)
(52) U.S. Cl. ...................... 570/171; 570/140
(58) Field of Classification Search ............... 570/140, 570/171
See application file for complete search history.

(56) References Cited

U.S. PATENT DOCUMENTS

2001/0020110 A1 9/2001 Shintaku et al.
2001/0034459 A1 10/2001 Meudt et al.

OTHER PUBLICATIONS

A. Indolese, "Suzuki-Type Coupling of Chloroarenes with Arylboronic Acids Catalysed by Nickel Complexes", Tetrahedron Letters, vol. 38, No. 20, (1997), pp. 3513-3516.
T. Korn et al., "New Colbalt-Catalyzed Cross-Coupling Reactions of Heterocyclic Chlorides with Aryl and Heteroaryl Magnesium Halides", SYNLETT 2003, No. 12, pp. 1892-1894.
Gilber R. Rosa, et al. "A Superior Non-Symmetrical NCP Pincer Type Palladacycle Catalyst Precursor for the Coupling of Aryl Boronic Acids with Aryl Chlorides", Synthesis, Georg Thieme Verlag, Stuttgart, DE, No. 18, Dec. 18, 2003, pp. 2894-2897.

*Primary Examiner*—J. Parsa
(74) *Attorney, Agent, or Firm*—Sughrue Mion, PLLC

(57) ABSTRACT

The present invention provides a process for producing 4-(2-methylphenyl)benzotrifluoride, comprising reacting 4-chlorobenzotrifluoride with 2-methylphenylmagnesium chloride in the presence of cobalt-based catalyst and zinc salt.

7 Claims, No Drawings

PROCESS FOR PRODUCING 4-(2-METHYLPHENYL)BENZOTRIFLUORIDE

This nonprovisional application claims priority under 35 U.S.C. § 119(a) on Patent Application No. 2005-069785 filed in JAPAN on Mar. 11, 2005, the entire contents of which are hereby incorporated by reference.

FIELD OF THE INVENTION

The present invention relates to a process for producing 4-(2-methylphenyl)benzotrifluoride useful as an intermediate for medicines and agricultural chemicals.

BACKGROUND OF THE INVENTION 4-(2-methylphenyl)benzotrifluoride is a compound useful as an intermediate for medicines and agricultural chemicals, for example, CP-319340 and CP-467688 of the following formulae (EP944602-A, WO98/23593-A).

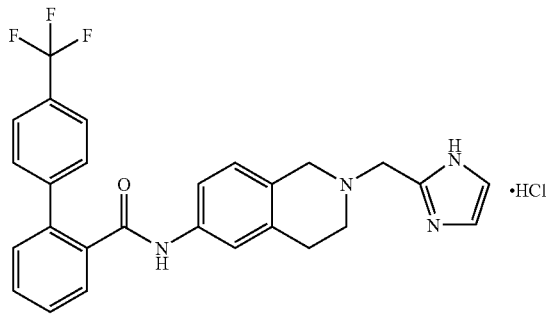

CP-319340

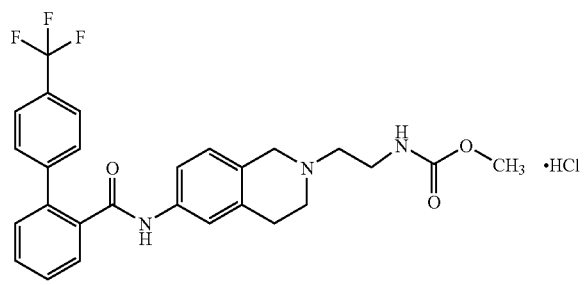

CP-467688

A production method by cross-coupling reaction aryl halides with corresponding aryl compounds has been reported, for example, by Tetrahedron Letters, 1997, vol. 38, no. 22, p. 3513–3516, JP2001-213816-A (patent family of US2001/0020110A1), JP2001-213817-A (patent family of US2001/0034459A1), and the like.

However, the methods have problems, such as use of expensive catalyst (e.g. Ni(dppf)Cl$_2$, Ni(PPh$_3$)Cl$_2$, Pd(dppf)Cl$_2$, Pd(PPh$_3$)Cl$_2$, and the like), use of expensive raw material or raw material which should be prepared through several steps, or the like. "dppf" and "PPh$_3$" mean "1,1'-bis(diphenylphosphino)ferrocene" and "triphenylphosphine", respectively.

SUMMARY OF THE INVENTION

An object of the present invention provides a process for producing 4-(2-methylphenylbenzotrifluoride, which uses inexpensive catalyst containing no phosphine derivative, and which can be applied simply, safely and at a industrial scale.

This and other objects of the present invention will be apparent from the following description.

The present invention relates to the followings:

<1> A process for producing 4-(2-methylphenyl)benzotrifluoride, comprising reacting 4-chlorobenzotrifluoride with 2-methylphenylmagnesium chloride in the presence of cobalt-based catalyst and zinc salt.

<2> The process according to <1>, wherein the reaction is carried out in the presence of aprotic polar organic solvent.

<3> The process according to <2>, wherein the aprotic polar organic solvent is a least one selected from N-methylimidazole, N,N-dimethylacetamide, 1,3-dimethyl-2-imidazolidinone and tetramethylurea.

<4> The process according to any of <1> to <3>, wherein the zinc salt is zinc chloride.

<5> The process according to any of <1> to <4>, wherein the cobalt-based catalyst is at least one selected from cobalt salt, cobalt(II) acetylacetonate and cobalt(III) acetylacetonate.

<6> The process according to any of <1> to <5>, wherein the reaction is carried out in a solvent.

<7> The process according to <6>, wherein the solvent is a mixture of aprotic polar organic solvent and ether solvent.

DESCRIPTION OF PREFERRED EMBODIMENTS

The present invention will be illustrated in detail below.

4-(2-methylphenyl)benzotrifluoride can be produced by reacting 4-chlorobenzotrifluoride with 2-methylphenylmagnesium chloride in the presence of cobalt-based catalyst and zinc salt. The reaction is so called cross-coupling reaction between 4-chlorobenzotrifluoride and 2-methylphenylmagnesium chloride in the presence of cobalt-based catalyst and zinc salt. Specifically, 4-(2-methylphenyl)benzotrifluoride can be produced, for example, by mixing cobalt-based catalyst, zinc salt, 4-chlorobenzotrifluoride and 2-methylphenylmagnesium chloride in a solvent, preferably with stirring the mixture. The addition order of the reagents is not particularly limited, and they may be added sequentially or simultaneously, and a procedure of dropping a solution of 2-methylphenylmagnesium chloride into a mixture of cobalt-based catalyst, zinc salt and 4-chlorobenzotrifluoride in a solvent is preferable.

4-Chlorobenzotrifluoride, cobalt-based catalyst and zinc salt are commercially available. 2-Methylphenylmagnesium chloride can be preliminarily produced by a conventional method, for example, by mixing magnesium and o-chlorotoluene in an inert solvent such as tetrahydrofuran.

Examples of the cobalt-based catalyst include cobalt salt, cobalt(II) acetylacetonate, cobalt(III) acetylacetonate, and the like. Examples of cobalt salt include cobalt chloride, cobalt bromide, cobalt acetate, cobalt sulfate, and the like. Cobalt chloride and cobalt(III) acetylacetonate are preferred. Cobalt-based catalyst may be used singly or in combination of at least two kind.

The amount of cobalt-based catalyst is usually 0.05 to 20 equivalents, preferably 0.1 to 10 equivalents per 100 equivalents of 4-chlorobenzotrifluoride.

Examples of zinc salt include zinc chloride, zinc bromide, and the like. Zinc chloride is preferred. Zinc salt may be used singly or in combination of at least two kind.

The amount of zinc salt is usually 5 to 50 equivalents, preferably 10 to 20 quivalents per 100 equivalents of 4-chlorobenzotrifluoride.

The process of the present invention is preferably conducted in the presence of aprotic polar organic solvent for attaining stably high yield. Examples of aprotic polar organic solvent include N,N-dimethylformamide, N-methylimidazole, N,N-dimethylacetamide, N-methyl-2-pyrrolidone, 1,3-dimethyl-2-imidazolidinone, tetramethylurea and the like. N-methylimidazole, N,N-dimethylacetamide, 1,3-dimethyl-2-imidazolidinone and tetramethylurea are preferred, and N,N-dimethylacetamide and 1,3-dimethyl-2-imidazolidinone are more preferred. The aprotic polar organic solvent may be used singly or in combination of at least two kind.

The amount of the aprotic polar organic solvent is usually 5 to 200 equivalents, preferably 20 to 100 equivalents per 100 equivalents of 4-chlorobenzotrifluoride.

The process of the present invention is usually conducted in a solvent. The solvent used in the present reaction is not particularly limited as long as it does not disturb the reaction. The solvent used in the present reaction may be the aprotic polar organic solvent, other solvent inactive to the reaction, a mixture of the aprotic polar organic solvent and at least one other solvent inactive to the reaction. Examples of the solvent inactive to the reaction include ether solvents, mixed solvents of ether solvents with other solvents, and the like. The solvent consisting essentially of a mixture of the aprotic polar organic solvent and the ether solvent is preferred.

The amount of the solvent used in the present reaction varies depending on the kind and amount of reagents used in the present reaction and is usually 3 to 30 parts by weight, preferably 4 to 15 parts by weight per 1 part of 4-chlorobenzotrifluoride.

Examples of the ether solvent mentioned above include tetrahydrofuran, diisopropyl ether, tert-butyl methyl ether, and the like, and tetrahydrofuran (THF) is preferred. The ether solvent may be used singly or in combination of at least two kind.

The solvent inactive to the reaction other than ether solvents may be organic solvents not reacting with 2-methylpheylmagnesium chloride used in the present invention. Examples thereof include aromatic hydrocarbons such as toluene, xylene, and the like.

The reaction temperature and reaction time vary depending on the kind and amount of catalyst and zinc salt to be used, and if necessary, on the kind and amount of solvent and the like. The reaction temperature is usually 0 to 70° C., preferably 10 to 60° C., and the reaction time is usually 0.5 to 20 hours, preferably 3 to 15 hours. When 2-methyphenylmagnesium chloride is added dropwise, its addition time varies depending on its amount, and the dropwise addition is conducted usually in 0.5 to 10 hours.

It is preferable that this reaction is usually conducted in an inert gas atmosphere such as a nitrogen, argon, and the like. The pressure of the above-mentioned inert gas is not particularly limited and usually, an atmospheric pressure is advantageous.

Isolation of the objective compound after the reaction can be conducted by a usual isolation method, and 4-(2-methylphenyl)benzotrifluoride can be isolated, for example, by adding hydrochloric acid to the reaction mixture, stirring the added mixture, performing phase-separation, then, washing the resultant organic layer with sodium chloride solution and the like, concentrating the washed organic layer, and conducting distillation. Further, the purity of 4-(2-methylphenyl)benzotrifluoride can be enhanced by performing a treatment with activated carbon, silica gel, alumina, and the like.

The resultant 4-(2-methylphenyl)benzotrifluoride can be changed to CP-319340 or CP-467688 which is a useful medicine, by converting methyl group to carboxyl group by an ordinary method, then, using a method according to U.S. Pat. No. 5,919,795, WO9640640-A, EP944602-A, WO9823593-A, and the like.

It should be construed that embodiments disclosed here are examples in all aspects and not restrictive. It is intended that the scope of the present invention is determined not by the above descriptions but by appended Claims, and includes all variations of the equivalent meanings and ranges to the Claims. The present invention will be described more specifically by way of examples, which are not construed to limit the scope of the present invention.

EXAMPLE 1

Into a 100 ml four-necked flask, were charged THF (13.54 g), cobalt(III) acetylacetonate (1.34 g, 3.75 mmol), anhydrous zinc(II) chloride (1.02 g, 7.5 mmol), 4-chlorobenzotrifluoride (13.54 g, 75 mmol) and N,N-dimethylacetamide (1.95 g, 22.5 mmol), and the temperature was adjusted to 60 to 65° C. Into the mixture, THF solution of 2-methylphenylmagnesium chloride (46.03 g, 112.5 mmol) was added dropwise for about 8 hours while keeping the inner temperature at 60 to 65° C. The reaction liquid was stirred for 1 hour at the same temperature, then, 4-(2-methylphenyl)benzotrifluoride was quantified by HPLC using biphenyl as in internal standard substance, to find out that its amount obtained was 16.18 g. The yield of 4-(2-methylphenyl)benzotrifluoride based on 4-chlorobenzotrifluoride was 91.29%.

HPLC Analysis Conditions

Column: SUMIPAX A212 ODS 6 mm i.d.×15 cm

Mobile phase: A liquid; 0.1% acetic acid aqueous solution, B liquid; acetonitrile

| Gradient conditions | | | | |
|---|---|---|---|---|
| Time (minute) | 0 | 10 | 30 | 40 |
| B (volume ratio %) | 60 | 60 | 80 | 80 |

Column temperature: 40° C.

Detection method/wavelength: UV/254 nm

Analysis time: 40 minutes

Flow rate: 1.0 mL/min

Retention time:

4-chlorobenzotrifluoride; about 14.9 minutes, biphenyl (internal standard); about 17 minutes, 4-(2-methylphenyl)benzotrifluoride; about 28.5 minutes $^1$H-NMR (400 MHz, CDCl$_3$) δ; 7.66 (brd, J=8.3 Hz, 2H), 7.42 (brd, J=8.3 Hz, 2H), 7.28–7.18 (m, 4H), 2.25 (d, J=3.4 Hz, 3H)

EXAMPLE 2

The reaction and HPLC quantification were conducted in the same manner as in Example 1 except that the amount of cobalt(III) acetylacetonate, N,N-demethylacetamide and THF solution of 2-methylphenylmagnesium chloride were changed to 0.14 g (0.375 mol), 6.50 g (75 mmol), and 46.29 g (112.5 mmol), respectively.

The amount of 4-(2-methylphenyl)benzotrifluoride obtained was 15.49 g. The yield of 4-(2-methylphenyl) benzotrifluoride based on 4-chlorobenzotrifluoride was 87.42%.

EXAMPLE 3

The reaction and HPLC quantification were conducted in the same manner as in Example 1 except that 1,3-dimethyl-2-imidazolidinone (1.71 g, 15 mmol) was used instead of N,N-dimethylacetamide (1.95 g, 22.5 mmol).

The amount of 4-(2-methylphenyl)benzotrifluoride obtained was 15.46 g. The yield of 4-(2-methylphenyl) benzotrifluoride based on 4-chlorobenzotrifluoride was 87.23%.

EXAMPLE 4

The reaction and HPLC quantification were conducted in the same manner as in Example 1 except that N-methylimidazole (1.24 g, 22.5 mmol) was used instead of N,N-dimethylacetamide (1.95 g, 22.5 mmol), and that the amount of THF solution of 2-methylphenylmagnesium chloride was changed to 49.83 g (127.5 mmol).

The amount of 4-(2-methylphenyl)benzotrifluoride obtained was 13.64 g. The yield of 4-(2-methylphenyl) benzotrifluoride based on 4-chlorobenzotrifluoride was 76.99%.

EXAMPLE 5

The reaction and HPLC quantification were conducted in the same manner as in Example 1 except that anhydrous cobalt(II) chloride (0.19 g, 1.5 mmol) was used instead of cobalt(III) acetylacetonate (1.34 g, 3.75 mmol), and that the amount of N,N-dimethylacetamide and THF solution of 2-methylphenylmagnesium chloride were changed to 2.60 g (30 mmol) and 46 29 g (112.5 mmol), respectively.

The amount of 4-(2-methylphenyl)benzotrifluoride obtained was 15.42 g. The yield of 4-(2-methylphenyl) benzotrifluoride based on 4-chlorobenzotrifluoride was 87.05%.

Comparative Example 1

The reaction and HPLC quantification were conducted in the same manner as in Example 1 except anhydrous zinc(II) chloride was not used, and that the amount of THF solution of 2-methylphenylmagnesium chloride was changed to 46.12 g (112.5 mmol).

The amount of 4-(2-methylphenyl)benzotrifluoride obtained was 2.86 g. The yield of 4-(2-methylphenyl)benzotrifluoride based on 4-chlorobenzotrifluoride was 16.17%.

EXAMPLE 6

The reaction and HPLC quantification were conducted in the same mariner as in Example 5 except that the amount of anhydrous cobalt(II) chloride, N,N-dimethylacetamide and THF solution of 2-methylphenylmagnesium chloride were changed to 0.05 g (0.375 mmol), 6.50 g (75 mmol) and 46.12 g (112.5 mmol), respectively.

The amount of 4-(2-methylphenyl)benzotrifluoride obtained was 15.32 g. The yield of 4-(2-methylphenyl) benzotrifluoride based on 4-chlorobenzotrifluoride was 86.50%.

EXAMPLE 7

The reaction and HPLC quantification were conducted in the same manner as in Example 5 except that tetramethythiourea (3.48 g, 30 mmol) was used instead of N,N-dimethylacetamide (2.60 g, 30 mmol), and that the amount of THF solution of 2-methylphenylmagnesium chloride was changed to 46.12 g (112.5 mmol).

The amount of 4-(2-methylphenyl)benzotrifluoride obtained was 14.71 g. The yield of 4-(2-methylphenyl) benzotrifluoride based on 4-chlorobenzotrifluoride was 83.00%.

The process according to the present invention can produce 4-(2-methylphenyl)benzotrifluoride simply, safely and industrially advantageously since expensive and phosphine derivative containing catalyst is not necessary to use.

What is claimed is:

1. A process for producing 4-(2-methylphenyl)benzotrifluoride, comprising reacting 4-chlorobenzotrifluoride with 2-methylphenylmagnesium chloride in the presence of cobalt-based catalyst and zinc salt.

2. The process according to claim 1, wherein the reaction is carried out in the presence of aprotic polar organic solvent.

3. The process according to claim 2, wherein the aprotic polar organic solvent is at least one selected from N-methylimidazole, N,N-dimethylacetamide, 1,3-dimethyl-2-imidazolidinone and tetramethylurea.

4. The process according to claim 1, wherein the zinc salt is zinc chloride.

5. The process according to claim 1, wherein the cobalt-based catalyst is at least one selected from cobalt salt, cobalt(II) acetylacetonate and cobalt(III) acetylacetonate.

6. The process according to claim 1, wherein the reaction is carried out in a solvent.

7. The process according to claim 6, wherein the solvent is a mixture of aprotic polar organic solvent and ether solvent.

* * * * *